United States Patent [19]

Kalasek

[11] 4,263,258
[45] Apr. 21, 1981

[54] STEAM-OPERATED STERILIZATION APPARATUS

[75] Inventor: Karl Kalasek, Vienna, Austria

[73] Assignee: Vereinigte Edelstahlwerke Aktiengesellschaft, Vienna, Austria

[21] Appl. No.: 56,610

[22] Filed: Jul. 11, 1979

[30] Foreign Application Priority Data

Jul. 28, 1978 [AT] Austria ............................... 5513/78

[51] Int. Cl.³ ............................ A61L 2/06; A61L 2/24
[52] U.S. Cl. ..................................... 422/113; 422/26; 422/114; 422/116; 422/298
[58] Field of Search ................. 422/26, 298, 299, 116, 422/114, 115, 292, 112, 113

[56] References Cited

U.S. PATENT DOCUMENTS

| | | | |
|---|---|---|---|
| 3,410,650 | 11/1968 | Bramson | 422/299 X |
| 3,450,487 | 6/1969 | Wallden | 422/26 |
| 3,494,725 | 2/1970 | Irons et al. | 422/26 |
| 4,164,538 | 8/1979 | Young et al. | 422/26 |

FOREIGN PATENT DOCUMENTS

| | | | |
|---|---|---|---|
| 269034 | 12/1963 | Australia | 422/26 |
| 1492481 | 1/1970 | Fed. Rep. of Germany | 422/26 |
| 7667 | 12/1897 | United Kingdom | 422/298 |

Primary Examiner—Barry Richman
Attorney, Agent, or Firm—Ernest F. Marmorek

[57] ABSTRACT

A steam-operated sterilization apparatus for sterilizing laundry, bandages, instruments and the like, includes a heat-insulated container, and a sterilization chamber disposed within the heat-insulated container. A space between the heat-insulated container and the sterilization chamber is filled with a fluid acting as a carrier of heat. A heating device heats the fluid to a temperature above 100° C., and a water conduit, connected to a source of water, is disposed in the space for passing the water therethrough. The water conduit includes a water-evaporation section for converting the water into steam, and a steam-heating section for converting the steam into superheated steam. The water conduit communicates with the sterilization chamber for introducing the steam and the superheated steam thereinto, and a discharge device communicates with the sterilization chamber for at least condensing the steam and the superheated steam, and for discharging the condensate.

9 Claims, 4 Drawing Figures

STEAM-OPERATED STERILIZATION APPARATUS

BACKGROUND OF THE INVENTION

The invention relates to a steam-operated sterilization apparatus for laundry, bandages, instruments and the like.

Until about the year 1930 laundry, bandages and instruments were sterilized exclusively at a temperature of 100° C. Particularly the sterilization of laundry and bandages was accomplished in streaming steam having a temperature of 100° C., and instruments were sterilized in boiling water. Water boilers for instruments have even been in use up till about 1960.

In order to improve the killing of any germs, and to shorten the sterilization time, sterilization was accomplished after 1930 increasingly by using either stationary or streaming saturated steam having a temperature of 120° C., and since about 1961 by using saturated steam having a temperature of between 134° C. to 140° C. The increase of the sterilization temperature also necessarily brought about an increase in the steam pressure. The sterilization temperature used mostly throughout the world today of 134° C. corresponds, for example to a steam pressure of 2.2 bar.

The conventional sterilization devices used up to now, which have been operated with saturated steam having a temperature above 100° C., are therefore equipped with a steam boiler for generating the steam, and a container for the steam, serving as a sterilization chamber; the steam container must comply with strict legal rules, as both the steam boiler and the steam container are subject to official inspection. Nevertheless, both the steam container and the steam boiler still remain a source of danger and in practice considerable personal and material damage has been caused by explosions.

SUMMARY OF THE INVENTION

It is therefore an object of the present invention to devise a sterilization apparatus which can be operated under its own steam temperature at above 100° C., without the need of a steam boiler and any auxiliary space-consuming and expensive gear used with such boiler. A further development of the invention results in a sterilization chamber which avoids the necessity of being subjected to official inspection.

The above object is achieved by providing a steam-operated sterilization apparatus for sterilizing laundry, bandages, instruments and the like, which includes a heat-insulated container, and a sterilization chamber disposed within the heat-insulated container. A space is defined between the heat-insulated container and the sterilization chamber, which is filled with a fluid acting as a carrier of heat. The apparatus includes a heating device operable for heating the fluid to a temperature above 100° C., a water conduit, which may be connected to a source of water and disposed in the space for passing the water therethrough, which conduit includes a water-evaporation section for converting the water into steam, and a steam-heating section for converting the steam into superheated steam. The water conduit communicates with the sterilization chamber for introducing the steam and the superheated steam thereinto, and as discharge device communicates with the sterilization chamber for at least condensing the steam and the superheated steam, and for discharging the condensate.

In a boilerless sterilization apparatus of the above type, the steam is generated by heat transfer from the heated carrier of heat, to water passing in a conduit immersed in the carrier of heat, the water being heated in a first section of this conduit to a boiling temperature and evaporated, the resulting steam being superheated in a second section of the conduit before it enters the sterilization chamber. The water-filled inner chamber of the conduit system therefore occupies only a fraction of a predetermined volume, which predetermined volume, according to statute, is subjected to strict supervision in the case of boilers, so that the sterilization apparatus of the present invention is not subject to such supervision. Depending whether or not a throttling of the steam takes place in the discharge conduit, or whether the steam may be freely discharged along with the condensate, there results either an operation above atmospheric pressure, using saturated steam at a temperature above 100° C., where the sterilization chamber is implemented as a pressure container, or there results an operation at atmospheric pressure using superheated and non-saturated steam, where implementation of the sterilization chamber as a pressure chamber is not required.

As the germ-killing capability of the unsaturated or superheated steam is smaller than that of the saturated steam, the sterilization time, when operating with unsaturated or superheated steam is longer, than that required when operating with saturated steam, as the killing of germs in the case of superheated steam is accomplished partially by unsaturated steam. The advantage of an entirely pressure-free operation must therefore be weighed in relation to a required trade-off with respect to sterilization time. If a short sterilization time is of primary interest, then operation by means of saturated steam is recommended; otherwise an operation with superheated or unsaturated steam is indicated.

When using sterilization devices for laundry, bandages or the like, the air contained in the pores of the goods to be sterilized must be sucked out by evacuation of the sterilization chamber, to permit a subsequent penetration of steam into the pores. On the other hand, following sterilization, the sterilized goods must be dried by evacuation of the sterilization chamber, and the pressure in the sterilization chamber must be equalized by means of newly sucked-in and substantially germ-free air. For this reason it is usual to generate the partial vacuum with the aid of a suitable suction pump in the sterilization chamber, so as to accomplish drying by partial vacuum.

Within the scope of the present invention, the use of a suction pump of this type, which consumes valuable space and causes an undesired high noise level in the operating room, can be avoided, by providing cooling means operable with a cooling fluid and communicating with the sterilization chamber, for cooling the steam-heated chamber, thereby introducing a partial vacuum therein, and by providing programmable control means for automatically actuating the cooling means upon a predetermined temperature being reached in the discharge means, and for simultaneously shutting off the source of water to the water-conducting means, and closure means operable to close the discharge device or means, and actuatable upon the partial vacuum occurring in the sterilization chamber; the cooling means is advantageously arranged to be automatically shut down, and the source of water is advantageously arranged to be automatically supplied to the water conduit or water-conducting means by the control means following a predetermined time interval.

The temperature extends preferably from about 132° C. to about 140° C., and the predetermined time interval is preferably presettable.

The actuation of the cooling means and its subsequent shut-down preferably includes a cooling cycle, and the programmable control means is preferably programmable for a plurality of the cooling cycles.

The sterilization chamber is preferably operable for a predetermined sterilization time, and the air-supply means is preferably connected to the sterilization chamber for the supply of filtered and substantially germ-free air; the air supply means may be actuated by the control means following completion of the sterilization time.

It is advantageous if a controllable throttle valve is provided for throttling the supply of the steam and of the superheated steam passing through the discharge means.

The water-conducting means preferably includes first and second independently operable water-supply devices.

The first and second water-supply devices may be implemented as either first and second water-supply pumps of different respective output ratings, or as a single water supply pump having a common check valve and first and second separately controllable outputs, including first and second separately controllable throttle valves, respectively.

The water-evaporating section is advantageously disposed substantially horizontally below the sterilization chamber, and at least a part of the steam-heating section is preferably disposed substantially vertically on one side of the sterilization chamber; the remaining part of the steam-heating section is advantageously disposed above the sterilization chamber.

The invention also encompasses a process of sterilizing laundry, bandages, instruments, and the like with the aid of a sterilization apparatus, including a sterilization chamber, the steps including (a) placing goods to be sterilized into the sterilization chamber, (b) selectably supplying steam and superheated steam to the sterilization chamber for a predetermined time period, (c) cooling the sterilization chamber upon the sterilization chamber having reached a predetermined temperature, (d) simultaneously with the cooling step shutting off the selective supply of the steam and superheated steam to the sterilization chamber, so that at least a partial vacuum is created in the sterilization chamber, (e) thereafter repeating steps (b) through (d) a predetermined number of times, and subsequently removing the sterilized goods from the sterilization chamber.

As will be explained later, in a sterilization device of the aforesaid kind, it is possible prior to the commencement of sterilization to initiate several cooling cycles by the program control device, which in turn evacuates the sterilization chamber and consequently sucks out the air from the porous goods to be sterilized in steps. At the completion of the sterilization time substantially germ-free air can be supplied to the chamber for the purpose of pressure equalization, and to dry the goods to be sterilized.

The inventive process therefore optionally includes the step of supplying filtered and substantially germ-free air to the sterilization chamber following steps (c) through (d), so that the goods in the sterilization chamber are at least being partially dried.

BRIEF DESCRIPTION OF THE DRAWINGS

For a fuller understanding of the nature and objects of the invention, reference should be had to the following detailed description, taken in connection with the accompanying drawings in which.

DESCRIPTION OF THE PREFERRED EMBODIMENTS

Figure 1:
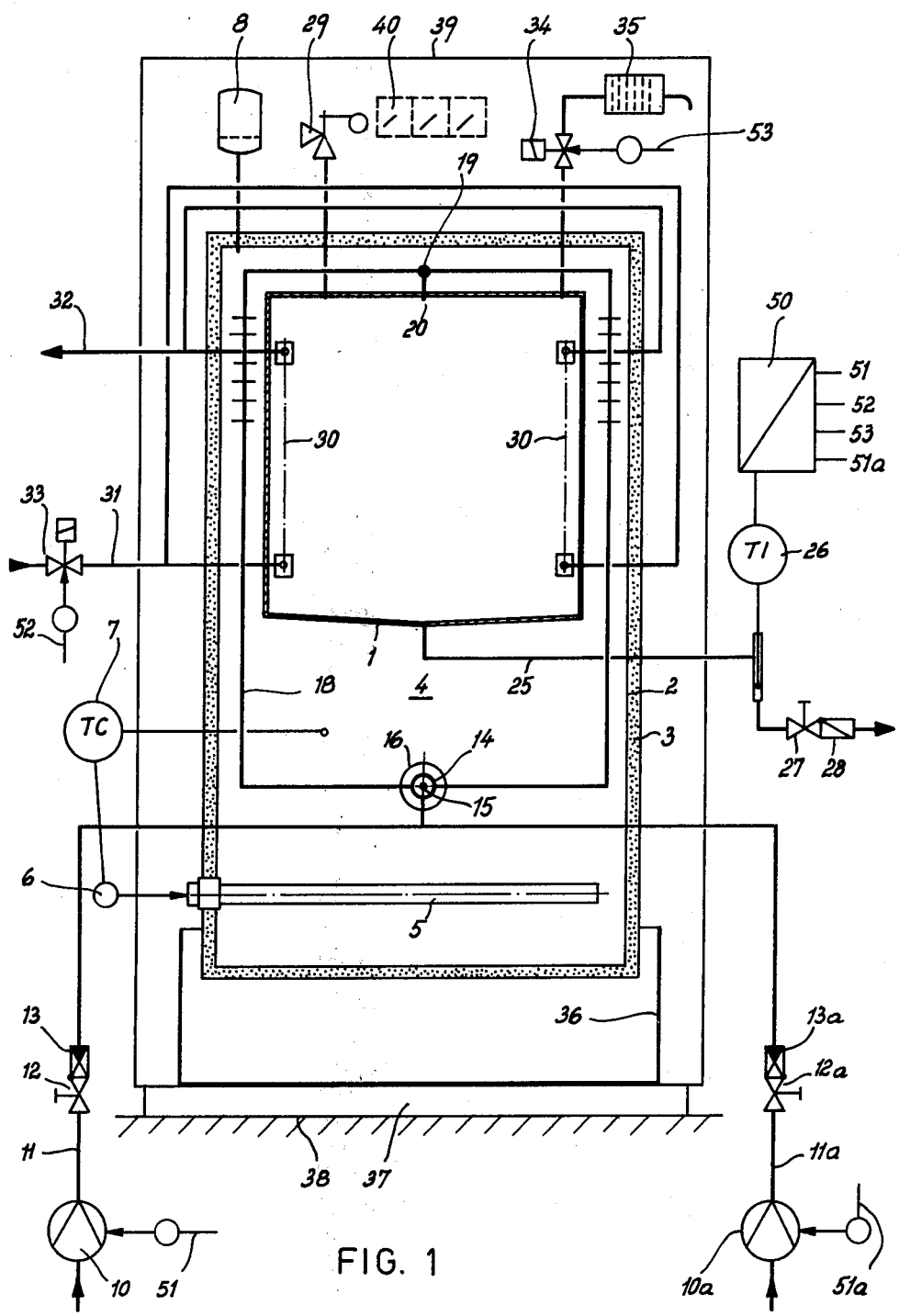
FIG. 1 shows a vertical section through the sterilization apparatus according to the present invention.

Referring now to the drawing, the sterilization chamber 1, which is accessible through a (non-illustrated) door, is disposed within a metallic container 2, the container 2 being lined with a heat-insulating layer 3 and filled with a fluid carrier of heat 4, preferably a so-called heat-carrying oil. In the lower portion of the container 2 there is disposed a heating means 5 surrounded by the carrier of heat 4, which includes (non-illustrated) electrical supply leads passing through an electrically controlled switch 6. The heating device 5 is controlled with the aid of a thermostat 7, so as to maintain the temperature of the heat-carrier 4 constant within the container 2. The container 2 includes on its upper portion a vessel 8 for receiving any expanding portion of the fluid heat-carrier 4.

Figure 2:
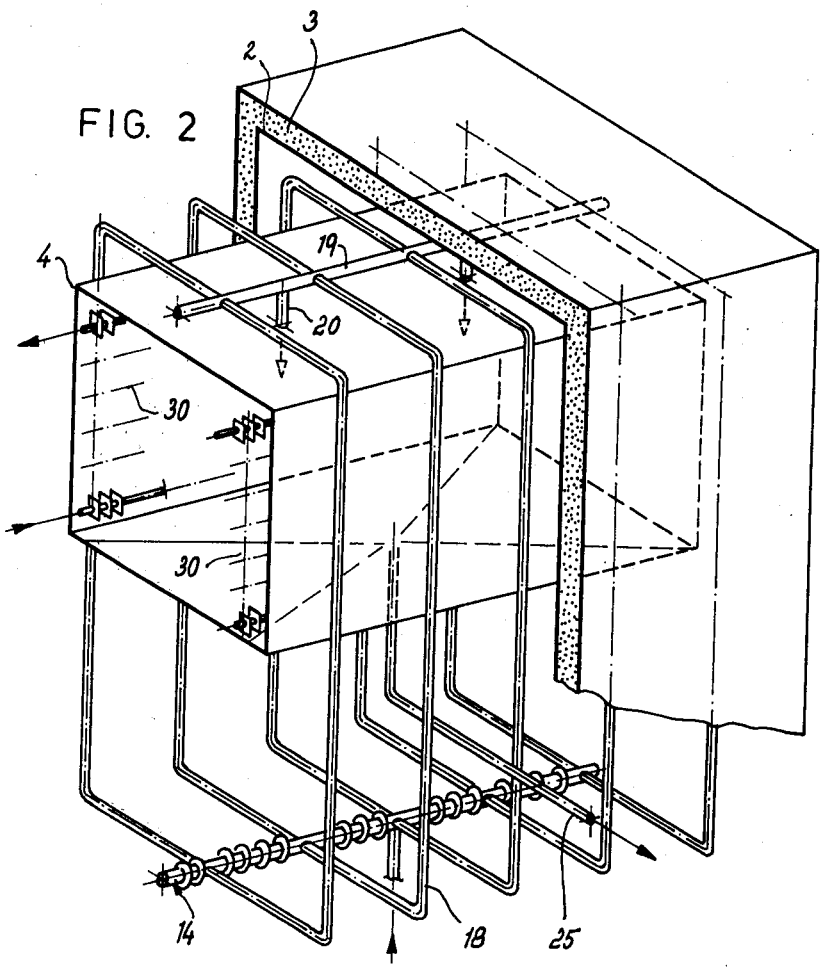
FIG. 2 shows a perspective view of the main components of the present apparatus in partial section.
Figure 3:
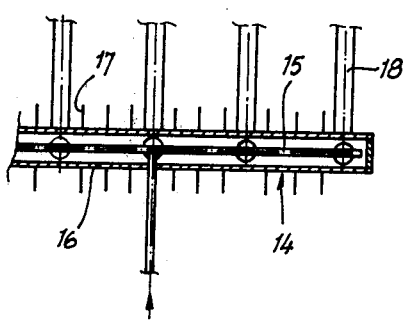
FIG. 3 shows a schematic longitudinal section through the steam-generating section of the apparatus.

In FIG. 1 there is further shown an electrically driven water pump 10 for supplying water from a water source to the apparatus, which includes a conduit 11 operable under pressure, and an adjustment valve 12, as well as a check valve 13. The adjustment valve 12 serves to adjust the output of the pump 10 according to the desired sterilization condition, as will be described later. The conduit 10 communicates with a water-conducting system within the container 2, namely a water-evaporating section 14, which is shown schematically in FIG. 3 in logitudinal section on a larger scale, and which consists of an inner spray tube 15, and an outer coaxial tube 16, provided with ribs 17. To the outer tube 16, as can be seen best from FIG. 2, there are coupled several conduits 18 disposed parallel to one another, which progress from the water-evaporating section 14, the water-evaporating section 14 being disposed below the sterilization chamber 1, and pass along opposite sides of the sterilization chamber 1 to a collecting conduit 19; the collecting conduit 19 is disposed above the sterilization chamber 1. A plurality of steam outlets 20 are disposed along the collecting conduit 1, which steam outlets 20 communicate with the sterilization chamber 1. The conduits 18 serve to further heat the steam, the pressure and the temperature of the steam being dependant on predetermined operating conditions, as will be explained later. The water-filled portions of the conduit systems 14 and 18 have such a small internal volume, that it is not subject to the inspection laws applicable to steam boilers. Any required amount of steam is generated from continuously supplied water in a continuous process, as is known from a rapid steam-generator, and the steam is not discharged from a storage boiler.

A discharge conduit 25, in which any steam discharged from the sterilization chamber 1 is condensed, communicates with the sterilization chamber 1 at about the center thereof, a contact thermometer 26 being postcoupled to the conduit 25, there being additionally disposed within the conduit 25 in the example shown a finely controllable throttle valve 27, as well as a check valve 28. The contact thermometer 26 is connected to an input of a programmable electric control device 50. The sterilization chamber is equipped on its upper portion with a safety valve 29.

Within the sterilization chamber 1 there are disposed on opposite sidewalls cooling devices 30, which in turn are connected in parallel to cooling water supply leads, and cooling water discharge leads 31 and 32, respectively. An electrically controlled openable and closeable valve 33 is provided in the cooling supply device 31. It is equally possible to dispose the cooling devices 30 outside of the sterilization chamber 1 in suitable containers, but communicating with the sterilization chamber 1.

The upper portion of the sterilization chamber 1 may be connected by means of an electrically controlled valve 34 with an air filter 35, to permit the entry of substantially germ-free air into the sterilization chamber 1.

The drive motor of the water-supply pump 10, the cooling water control valve 33, and the control valve 34 for entry of substantially germ-free air into the sterilization chamber 1 are controlled by the control device 50 via control leads 51, 52 or 53; the contact thermometer 26 is connected to the input circuit of the control device 50.

The heat-insulated container 2 rests on the floor of a tub 36 by means of (non-illustrated) supports, which tub 36 receives any heat-carrying fluid 4 in the event the container 2 is leaking. The tub 36, in turn, rests on the floor 38 through its pedestal 37, and the entire sterilization apparatus is covered by means of a sheet steel container 39, on which there are disposed supervisory instruments 40, which instruments 40 are only shown schematically.

So as to render the sterilization apparatus always ready for operation, the fluid heat-carrier 4 may be continuously heated by means of the thermostatically controlled heating device 5. When sterilizing by means of saturated steam, the amount of supply water supplied to the sterilization apparatus per unit time is adjusted by means of the adjustment valve 12, and the temperature of the heat-carrier 4 is adjusted by means of the thermostat 7, so that there is obtained saturated steam in the sterilization chamber 1 having a temperature of, for example, 134° C. These adjustments remain unchanged during operation.

After the sterilization goods have been placed into the sterilization chamber 1, the sterilization chamber 1 is closed tightly. As a result of the heating of the enclosed air, a large portion thereof is expelled via the valve 27, and the open check valve 28. Then the water-supply pump 10 is actuated by the program control device 50 via the control lead 51, as a result of which a measured and predetermined supply of water is fed to the water-evaporation section 14, and to the steam-heating section 18.

When sterilizing instruments and other solid objects which are not porous, it is only necessary to complete a predetermined sterilization time, when the required sterilization temperature has been reached.

Following completion of the sterilization time, the pump 10 supplying the water is disconnected by the control device 50 via the control lead 51, and the valve 33 for the supply of the cooling water is opened. The steam condenses in the sterilization chamber 1 by the action of the cooling device 30, so that a partial vacuum is obtained in the sterilization chamber 1, which partial vacuum in turn causes the check valve 28 in the discharge conduit 25 to close. Thereafter the air-inlet valve 34 is opened by the control device 50 via the control conduit 53, so that substantially germ-free air is sucked into the sterilization chamber 1 through a sterilization filter 35, until equalization of pressure occurs, so that the sterilization chamber 1 can be opened, and the sterilized goods can be removed therefrom.

During the sterilization of laundry, bandages or similar porous material, entry of steam into the pores of the material must be made possible by expelling the air from the pores of the material. This is accomplished in the implementation shown in a particularly advantageous manner, by introducing the steam into the sterilization chamber, and condensing it several times prior to the sterilizing process proper. For this purpose the contact thermometer 26, which is postcoupled to the discharge conduit 25, provides a control impulse to the program control device 50 upon a predetermined temperature, for example, 100° C., being reached in the steam-condensate mixture; hence the water-supply pump 10 will be switched off via the control circuit 51, and the control valve 33 for the cooling water will be opened via the control circuit 52. As a result of switching in the cooling device 30, the steam condenses in the sterilization chamber 1, and a partial vacuum results therein, as the check valve 28 in the discharge circuit closes, as a result of which air is sucked out of the pores of the sterilizing goods and passes into its immediate environment. The control device 50 then switches in the water supply, and switches off the cooling water supply, which in turn causes steam to pass through the sterilization chamber 1, which steam takes along the air sucked from the pores of the sterilization goods as it passes therethrough. By repeating this process several times, the same effect is created as in known fractionating vacuum pump operations.

Subsequently, the water supply pump 10 is switched in by the control device 50 for the duration of the sterilization process proper, and the cooling water control valve 33 is shut off for the same period. Following completion of the sterilization time, while the goods are sterilized, for example, using saturated steam at a temperature of 134° C. and at a pressure of 2.2 bar, the control device 50 again turns off the water supply, switches on the cooling water supply via the control circuit 53, as well as the air inlet valve 34, so that the partial vacuum resulting as a result of condensation of the steam in the sterilization chamber 1 causes substantially germ-free air to be sucked into the sterilization chamber 1, until the pressure prevailing therein is equalized with the atmospheric pressure, so that the sterilization chamber 1 can be easily opened.

If it is desired to operate by means of superheated steam at atmospheric pressure, then the throttle valve 27 in the discharge conduit 25 can be dispensed with, so that the pressure in the sterilization chamber 1 corresponds to normal atmospheric pressure. By appropriate apportionment of the water being supplied, and by suitably selecting the temperature of the heat carrier 4, it is possible to reach a desired temperature of the superheated steam at the steam outlets 20.

The remaining operation of the apparatus remains substantially unchanged. It is an advantage of this implementation that it is not only possible to avoid the use of a steam boiler, but that a pressure container is no longer required by the particular implementation of the sterilization chamber.

During sterilization operations in hospitals it is desired to sterilize rubber gloves and other rubber parts, or parts composed of a similar temperature-sensitive material, and which is sterilized at relatively low temperatures, for example at about 120° C. In order to operate at such a relatively low temperature, it is only necessary to increase the amount of water being supplied per unit time. In order to permit a transition to a sterilization at a lower temperature without changing the adjustment of the pump, there is provided in the implementation shown a second pump 10 as an alternative to the pump 10, which can be switched in as required, and whose throttle valve 12a may be adjusted for an increased water supply. The pump 10a communicates with the water evaporation section 14 via a check valve 13a and a pressure conduit 11a in a similar manner as the pump 10, and the pump 10a may be switched in, and switched out, via a control conduit 51a.

Figure 4:
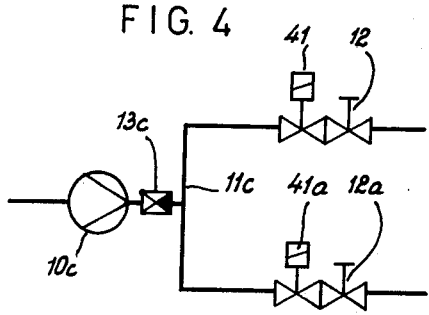
FIG. 4 shows an alternate version of the water-supply device of the apparatus.

An alternate implementation is shown in FIG. 4; in this version only a single water supply pump 10c is provided, which is coupled to the pressure conduit 11c via two parallel branches, there being disposed in the two parallel branches selectively actuable switching valves 41 and 41a, as well as differently preadjusted throttle valves 12 and 12a. A common check valve 13c is provided in the pressure conduit 11c.

The invention may be operated with various changes from the implementation examples shown. For example the carrier of heat may be also heated by external steam.

Having thus described the invention, what I claim as new and desire to be secured by Letters Patent is as follows:

1. A steam-operated sterilization apparatus for sterilizing laundry, bandages, instruments and the like, comprising in combination:
 a heat-insulated container,
 a sterilization chamber having a plurality of walls and being disposed within said heat-insulated container, said heat-insulated container completely surrounding said sterilization chamber and being spaced therefrom to define a space bordering all of said walls between said heat-insulated container and said sterilization chamber, said space being fillable with a fluid acting as a carrier of heat, the temperature of said sterilization chamber being thereby maintainable at the temperature of said fluid,
 heating means operable for heating said fluid to a temperature above 100° C., and for substantially maintaining it thereat,
 water-conducting means connectable to a source of water and disposed in said space for passing the water therethrough including a water-evaporation section for converting the water into steam, and a steam-heating section for converting the steam into superheated steam, said steam heating section communicating with said sterilization chamber for introducing the superheated steam thereinto,
 discharge means communicating with the atmosphere and said sterilization chamber for condensing the superheated steam, and for discharging the condensate and
 cooling means operable with a cooling fluid and disposed within said sterilization chamber, for cooling the steam-heated sterilization chamber, thereby introducing a partial vacuum therein, programmable control means for automatically actuating said cooling means upon a predetermined temperature being reached in said discharge means, and for simultaneously shutting off the source of water to said water-conducting means, and closure means operable to close said discharge means and actuatable upon said partial vacuum occuring in said sterilization chamber, said cooling means being arranged to be automatically shut down, and the source of water being arranged to be automatically supplied to said water-conducting means by said control means following a predetermined time interval.

2. A steam-operated sterilization apparatus as claimed in claim 1, wherein said predetermined time interval is presettable.

3. A steam-operated sterilization apparatus as claimed in claim 1, wherein the actuation of said cooling means and its subsequent shut-down comprises a cooling cycle, and wherein said programmable control means is programmable for a plurality of said cooling cycles.

4. A steam-operated sterilization apparatus as claimed in claim 1, wherein said sterilization chamber is operable for a predetermined sterilization time, and further comprising air-supply means connected to said sterilization chamber for the supply of filtered and substantially germ-free air, said air supply means being actuatable by said control means following said sterilization time.

5. A steam-operated sterilization apparatus as claimed in claim 1, wherein said water-conducting means include a single water-supply pump having a common check valve and first and second separately controllable outputs, including first and second separately controllable throttle valves, respectively.

6. A steam-operated sterilization apparatus as claimed in claim 1, wherein said water-evaporating section is disposed substantially horizontally below said sterilization chamber, wherein at least a part of said steam-heating section is disposed substantially vertically on one side of said sterilization chamber, and wherein the remaining part of said steam-heating section is disposed above said sterilization chamber.

7. A steam-operated sterilization apparatus as claimed in claim 1, wherein said water-conducting means includes first and second independently operable water-supply pumps.

8. A steam-operated sterilization apparatus as claimed in claim 7, wherein said first and second water-supply pumps have different respective output ratings.

9. A steam-operated sterilization apparatus for sterilizing laundry, bandages, instruments and the like, comprising in combination:
 a heat-insulated container,
 a sterilization chamber having a plurality of walls and being disposed within said heat-insulated container, said heat-insulated container completely surrounding said sterilization chamber and being spaced therefrom to define a space bordering all of said walls between said heat-insulated container and said sterilization chamber, said space being fillable with a fluid acting as a carrier of heat, the temperature of said sterilization chamber being thereby maintainable at the temperature of said fluid, heating means operable for heating said fluid to a temperature from about 132° C. to about 140° C., and for substantially maintaining it thereat, fluid overflow receiving means communicating with said space for receiving any expanding portion of the fluid heated by said heating means, water-conducting means connectable to a source of water and disposed in said space for passing the water therethrough including a water-evaporation section for converting the water into steam, and a steam-heating section for converting the steam into superheated steam, said steam heating section communicating with said sterilization chamber for introducing the superheated steam thereinto, discharge means communicating with the atmosphere and said sterilization chamber for condensing the superheated steam, and for discharging the condensate and cooling means operable with a cooling fluid and disposed within said sterilization chamber for cooling the steam-heated sterilization chamber, thereby introducing a partial vacuum therein, programmable control means for automatically actuating said cooling means upon a predetermined temperature being reached in said discharge means, and for simultaneously shutting off the source of water to said water-conducting means, and closure means operable to close said discharge means and actuatable upon said partial vacuum occuring in said sterilization chamber, said cooling means being arranged to be automatically shut down, and the source of water being arranged to be automatically supplied to said water-conducting means by said control means following a predetermined time interval.

* * * * *